US008608375B2

(12) United States Patent
Rhodes

(10) Patent No.: US 8,608,375 B2
(45) Date of Patent: Dec. 17, 2013

(54) METHOD AND SYSTEM TO MEASURE TEMPERATURE OF GASES USING COHERENT ANTI-STOKES DOPPLER SPECTROSCOPY

(75) Inventor: Mark Rhodes, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 403 days.

(21) Appl. No.: 12/905,958

(22) Filed: Oct. 15, 2010

(65) Prior Publication Data

US 2012/0093194 A1 Apr. 19, 2012

(51) Int. Cl.
 *G01J 5/08* (2006.01)
 *G01K 11/00* (2006.01)
 *G01J 3/10* (2006.01)

(52) U.S. Cl.
 USPC ........... 374/161; 374/130; 374/121; 374/141; 73/25.01; 356/301

(58) Field of Classification Search
 USPC ......... 374/120, 121, 130–133, 141, 100, 161; 367/94; 422/82.05, 82.12, 83, 84, 89; 436/147, 161, 900
 See application file for complete search history.

(56) References Cited

U.S. PATENT DOCUMENTS

| 4,018,529 | A | * | 4/1977 | Barrett ............................ 356/45 |
| 4,270,864 | A | * | 6/1981 | Barrett et al. ................. 356/301 |
| 4,284,354 | A | * | 8/1981 | Liao .............................. 356/301 |
| 4,430,291 | A | | 2/1984 | Chi |
| 4,440,714 | A | | 4/1984 | Rose |
| 4,492,862 | A | * | 1/1985 | Grynberg et al. ............. 250/255 |
| 4,624,561 | A | * | 11/1986 | Exton .......................... 356/28.5 |
| 4,663,110 | A | | 5/1987 | Cheng |
| 4,698,198 | A | | 10/1987 | Gruen |
| 5,160,696 | A | | 11/1992 | Bowman |
| 5,694,477 | A | * | 12/1997 | Kole .............................. 381/111 |
| 5,717,774 | A | * | 2/1998 | Kole .............................. 381/111 |
| 5,786,893 | A | * | 7/1998 | Fink et al. ...................... 356/301 |
| 6,391,647 | B1 | * | 5/2002 | Sperling et al. ............... 436/171 |
| 6,676,402 | B1 | | 1/2004 | Early et al. |
| 2002/0057754 | A1 | | 5/2002 | Stauffer et al. |
| 2005/0157832 | A1 | | 7/2005 | Nordberg |
| 2006/0002503 | A1 | | 1/2006 | Ougouag et al. |
| 2006/0280217 | A1 | | 12/2006 | Zervas et al. |
| 2008/0285008 | A1 | * | 11/2008 | Vachss et al. ................ 356/5.01 |

FOREIGN PATENT DOCUMENTS

| JP | 61184427 A | * | 8/1986 |
| JP | 2002277327 A | * | 9/2002 |
| WO | WO 2009/058185 A2 | | 5/2009 |

OTHER PUBLICATIONS

Tolles et al., "A review of the Theory and Application of Coherent Anti-Stokes Raman Spectrocsopy (CARS)," Applied Spectroscopy, vol. 31, Issue 4, Jul. 1977, pp. 253-272.

* cited by examiner

*Primary Examiner* — Gail Verbitsky
(74) *Attorney, Agent, or Firm* — Kilpatrick Townsend & Stockton

(57) ABSTRACT

A method of measuring a temperature of a noble gas in a chamber includes providing the noble gas in the chamber. The noble gas is characterized by a pressure and a temperature. The method also includes directing a first laser beam into the chamber and directing a second laser beam into the chamber. The first laser beam is characterized by a first frequency and the second laser beam is characterized by a second frequency. The method further includes converting at least a portion of the first laser beam and the second laser beam into a coherent anti-Stokes beam, measuring a Doppler broadening of the coherent anti-Stokes beam, and computing the temperature using the Doppler broadening.

10 Claims, 5 Drawing Sheets

METHOD AND SYSTEM TO MEASURE TEMPERATURE OF GASES USING COHERENT ANTI-STOKES DOPPLER SPECTROSCOPY

STATEMENT AS TO RIGHTS TO INVENTIONS MADE UNDER FEDERALLY SPONSORED RESEARCH OR DEVELOPMENT

The U.S. Government has rights in this invention pursuant to Contract No. DE-AC 52-07NA27344 between the U.S. Department of Energy and Lawrence Livermore National Security, LLC, for the operation of Lawrence Livermore National Laboratory.

BACKGROUND OF THE INVENTION

Projections by the Energy Information Agency and current Intergovernmental Panel on Climate Change (IPCC) scenarios expect worldwide electric power demand to double from its current level of about 2 terawatts electrical power (TWe) to 4 TWe by 2030, and could reach 8-10 TWe by 2100. They also expect that for the next 30 to 50 years, the bulk of the demand of electricity production will be provided by fossil fuels, typically coal and natural gas. Coal supplies 41% of the world's electric energy today, and is expected to supply 45% by 2030. In addition, the most recent report from the IPCC has placed the likelihood that man-made sources of $CO_2$ emissions into the atmosphere are having a significant effect on the climate of planet earth at 90%. "Business as usual" baseline scenarios show that $CO_2$ emissions could be almost two and a half times the current level by 2050. More than ever before, new technologies and alternative sources of energy are essential to meet the increasing energy demand in both the developed and the developing worlds, while attempting to stabilize and reduce the concentration of $CO_2$ in the atmosphere and mitigate the concomitant climate change.

Nuclear energy, a non-carbon emitting energy source, has been a key component of the world's energy production since the 1950's, and currently accounts for about 16% of the world's electricity production, a fraction that could—in principle—be increased. Several factors, however, make its long-term sustainability difficult. These concerns include the risk of proliferation of nuclear materials and technologies resulting from the nuclear fuel cycle; the generation of long-lived radioactive nuclear waste requiring burial in deep geological repositories; the current reliance on the once through, open nuclear fuel cycle; and the availability of low cost, low carbon footprint uranium ore. In the United States alone, nuclear reactors have already generated more than 55,000 metric tons (MT) of spent nuclear fuel (SNF). In the near future, we will have enough spent nuclear fuel to fill the Yucca Mountain geological waste repository to its legislated limit of 70,000 MT.

Fusion is an attractive energy option for future power generation, with two main approaches to fusion power plants now being developed. In a first approach, Inertial Confinement Fusion (ICF) uses lasers, heavy ion beams, or pulsed power to rapidly compress capsules containing a mixture of deuterium (D) and tritium (T). As the capsule radius decreases and the DT gas density and temperature increase, DT fusion reactions are initiated in a small spot in the center of the compressed capsule. These DT fusion reactions generate both alpha particles and 14.1 MeV neutrons. A fusion burn front propagates from the spot, generating significant energy gain. A second approach, Magnetic Fusion Energy (MFE), uses powerful magnetic fields to confine a DT plasma and to generate the conditions required to sustain a burning plasma and generate energy gain.

Important technology for ICF is being developed primarily at the National Ignition Facility (NIF) at Lawrence Livermore National Laboratory (LLNL), assignee of this invention, in Livermore, Calif. There, a laser-based inertial confinement fusion project designed to achieve thermonuclear fusion ignition and burn utilizes laser energies of 1 to 1.3 MJ. Fusion yields of the order of 10 to 20 MJ are expected. Fusion yields in excess of 200 MJ are could be expected to be required in central hot spot fusion geometry if fusion technology, by itself, were to be used for cost effective power generation. Thus, significant technical challenges remain to achieve an economy powered by pure ICF energy.

SUMMARY OF THE INVENTION

According to embodiments of the present invention, techniques related to measuring gas temperature are provided. More particularly, embodiments of the present invention relate to methods and systems for measuring the temperature of noble gases in a fusion reaction chamber. In a particular embodiment of the present invention, the temperature of xenon gas present in a plasma state in a fusion reaction chamber is measured using coherent anti-Stokes Doppler spectroscopy. The methods and systems described herein are applicable to the measurement of the temperature of hot, monatomic gases in hostile environments. Additionally, the methods and systems described herein are applicable to the measurement of trace amounts of monatomic gases in gas mixtures.

According to an embodiment of the present invention, a method of measuring a temperature of a noble gas in a chamber is provided. The method includes providing the noble gas in the chamber. The noble gas is characterized by a pressure and a temperature. The method also includes directing a first laser beam into the chamber and directing a second laser beam into the chamber. The first laser beam is characterized by a first frequency and the second laser beam is characterized by a second frequency. The method further includes converting at least a portion of the first laser beam and the second laser beam into a coherent anti-Stokes beam, measuring a Doppler broadening of the coherent anti-Stokes beam, and computing the temperature using the Doppler broadening.

According to another embodiment of the present invention, a system for measuring a temperature of a monatomic gas present in a chamber is provided. The system includes a first laser source operable to produce a first laser beam having a first frequency and first optics operable to direct the first laser beam into the chamber along a first optical path. The system also includes a second laser source operable to produce a second laser beam having a second frequency and second optics operable to direct the second laser beam into the chamber along a second optical path intersecting the first optical path at an intersection region. A coherent anti-Stokes beam is generated through a non-linear interaction with the monatomic gas at the intersection region and then propagates along a third optical path. The system further includes a detector disposed along a third optical path and a processor coupled to the detector.

Numerous benefits are achieved by way of the present invention over conventional techniques. For example, embodiments of the present invention provide methods and systems suitable for measuring temperatures of noble gases that are not available using conventional techniques. Data collected using embodiments of the present invention can be utilized to monitor performance of a fusion engine, control inputs provided to a fusion engine, and the like. These and other embodiments of the invention along with many of its advantages and features are described in more detail in conjunction with the text below and attached figures.

DETAILED DESCRIPTION OF SPECIFIC EMBODIMENTS

Embodiments of the present invention relate to fusion reaction chambers. Embodiments of the present invention are applicable to energy systems including, but not limited to, a Laser Inertial-confinement Fusion Energy (LIFE) engine, hybrid fusion-fission systems such as a hybrid fusion-fission LIFE system, a generation IV reactor, an integral fast reactor, magnetic confinement fusion energy (MFE) systems, accelerator driven systems and others. In some embodiments, the energy system is a hybrid version of the LIFE engine, a hybrid fusion-fission LIFE system, such as described in International Patent Application No. PCT/US2008/011335, filed Sep. 30, 2008, titled "Control of a Laser Inertial Confinement Fusion-Fission Power Plant", the disclosure of which is hereby incorporated by reference in its entirety for all purposes.

According to an embodiment of the present invention, methods and systems are provided for measuring the temperature of gases present in a gas-filled ICF reactor chamber. In ICF systems operating at high repetition rates (e.g., 13 Hz), measurement of the chamber temperature provides an important diagnostic for system performance.

Figure 1:
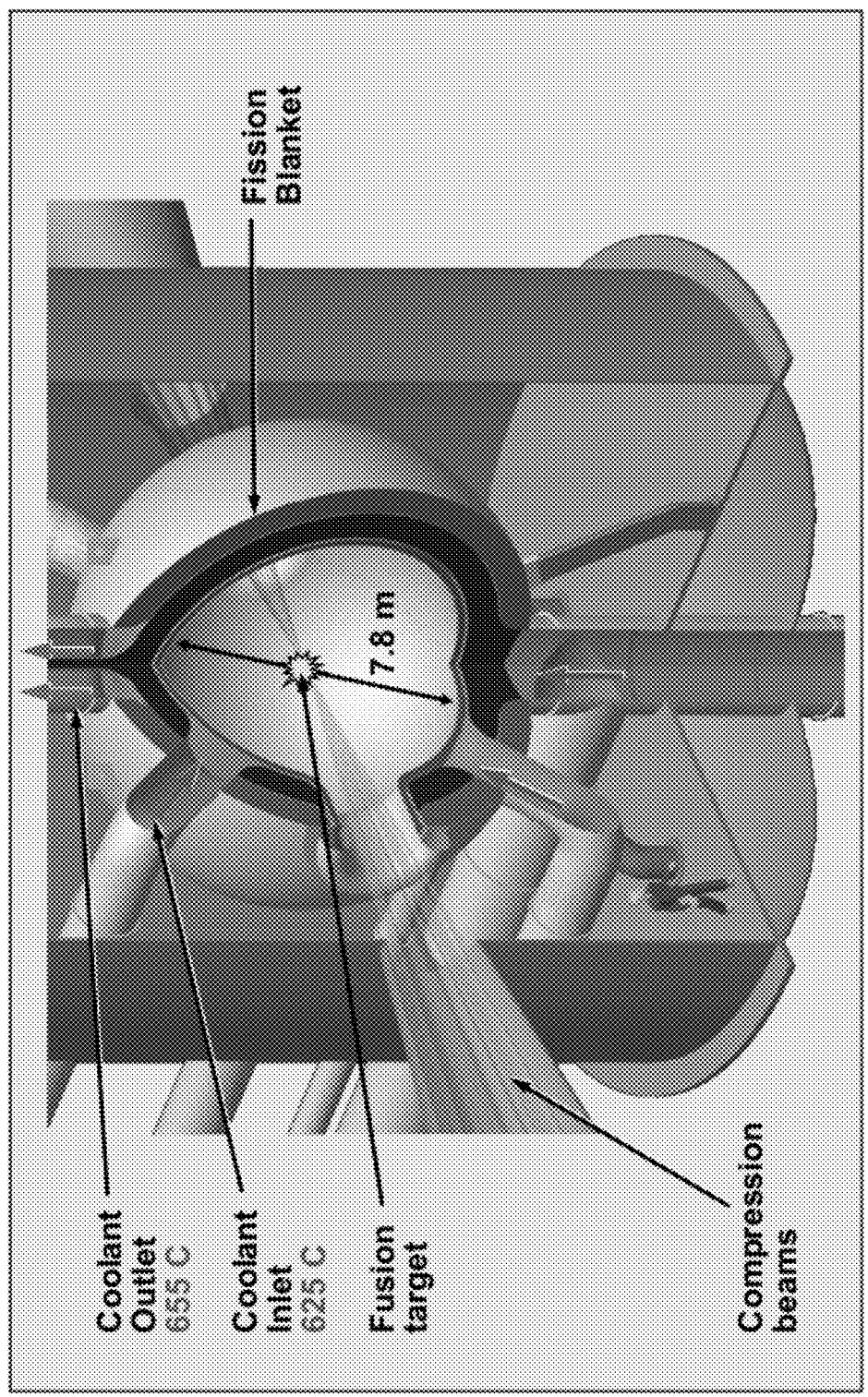
FIG. 1 is a simplified schematic diagram of a LIFE reaction chamber according to an embodiment of the present invention.

FIG. 1 is a simplified schematic diagram of a fusion reaction chamber according to an embodiment of the present invention. The fusion reaction chamber illustrated in FIG. 1 is not intended to limit the scope of embodiments of the present invention and is merely presented as an example chamber in which embodiments of the present invention can be implemented. Other chamber designs are also included within the scope of the present invention. The fusion reaction chamber, which can be a fast ignition fusion chamber, receives laser compression beams and ignition beams. The fusion target is illustrated in the center of the chamber and a fission blanket surrounds the chamber. The spherical chamber configuration illustrated in FIG. 1 enables uniform irradiation of the fission fuel in the fission blanket and uniform radiation damage to the chamber walls before replacement, thereby maximizing material utilization. Preferably, oxide dispersion strengthened ferritic steels are used for construction of the spherical engine chamber, with a solid first wall consisting of tungsten or tungsten-carbide armor. Such steel is less sensitive to displacement from lattice sites by neutron bombardment.

The chamber includes a layer of beryllium or lead as a neutron moderator and multiplier. A radial flow high-temperature lithium-containing coolant system, for example, using flibe ($2LiF+BeF_2$) or flinak ($LiF+NaF+KF$), includes multiple entrance ports, others not shown, as well as one or more exit ports. The coolant removes heat from the fission blanket and transports the heat to a Brayton energy conversion system. A high-rate fusion target fabrication and injection system, with target tracking and laser firing, introduces targets into the chamber at a high repetition rate. Additional description related to fusion reaction chambers are their operation is found in International Patent Application No. PCT/US2008/011335, incorporated by reference above.

The chamber is filled with xenon gas, other noble gases, or combinations thereof at an atomic density of approximately $1\times10^{16}$ cm$^{-3}$ to $3\times10^{16}$ cm$^{-3}$ (i.e., on the order of 0.5 Torr to 1 Torr). As an example, the fusion reaction chamber could utilize a xenon/krypton mixture. Other embodiments include both inert noble gases and other gas species including molecular gas species. The gas present in the chamber absorbs a significant portion of the x-ray energy produced by the fusion event and prevents essentially all ions emitted from the fusion targets from reaching the inner wall of the chamber. Thus, xenon, xenon/krypton mixtures, and the like serve as a first wall protector in the fusion reaction chamber illustrated in FIG. 1.

The hot gas cools via radiation on a timescale sufficiently long to prevent damage to the tungsten coated first wall. Thus, using the chamber gas as an energy absorber essentially turns a nanosecond burst of x-rays into a millisecond burst of heat, which can be accommodated via thermal conduction in the tungsten. The gas density is low enough to allow for propagation of the laser beams to the target. Because the gas absorbs energy produced by the fusion event, the temperature of the gas present in the chamber is high (e.g., 7,000K-20,000K). Measurement of the temperature of the noble gas at these high temperatures, for example, 8,000K is desirable.

In addition to fusion reaction chambers, noble gases are also widely used in various lasers system both as gain media (e.g. KrF lasers) and pump media (flashlamps). Thus, in addition to applications for temperature measurements of monatomic species in a plasma state in fusion reaction chambers, embodiments of the present invention are also applicable to the measurement of noble gas temperatures in other systems including noble gases at high temperatures.

According to embodiments of the present invention, the temperature of the xenon or other monatomic gas(es) present in the fusion reaction chamber is measured to provide chamber diagnostics, inputs to cooling systems, feedback data, or the like. Coherent anti-Stokes emission is a non-linear optical process that can occur in liquid and gaseous materials. An anti-Stokes emission signal is produced when two optical waves of different frequency propagate through a material with nonlinear properties. The anti-Stokes emission signal is proportional to the third-order optical susceptibility ($\chi_{3}$) of the material. Two different "beat" frequencies are produced in this nonlinear interaction: the down-shifted Stokes signal and the up-shifted anti-Stokes signal.

Coherent anti-Stokes Raman Spectroscopy (CARS) is a method to measure the temperature of molecular gases based on the vibrational resonances of the molecular gases. CARS differs from conventional Raman spectroscopy in several important ways. First, if the two source waves are coherent sources, such as lasers, the CARS signal is also coherent. It is produced at a predictable frequency and only in one particular direction. Since the CARS signal is at an up-shifted wavelength, it remains an optical wavelength and can be easier to detect than infrared Raman signals. CARS signal are typically orders of magnitude stronger than the down-sifted conventional Raman scattered signal.

CARS can be used to measure the temperature in hot gases that contain molecular species such as diatomic nitrogen ($N_2$) or carbon dioxide ($CO_2$). These methods rely on observing changes in the complex vibrational-mode spectra of the molecular species. Since monatomic gases lack vibrational resonances, CARS is not a suitable technique for temperature measurement of these monatomic gases.

Figure 2:
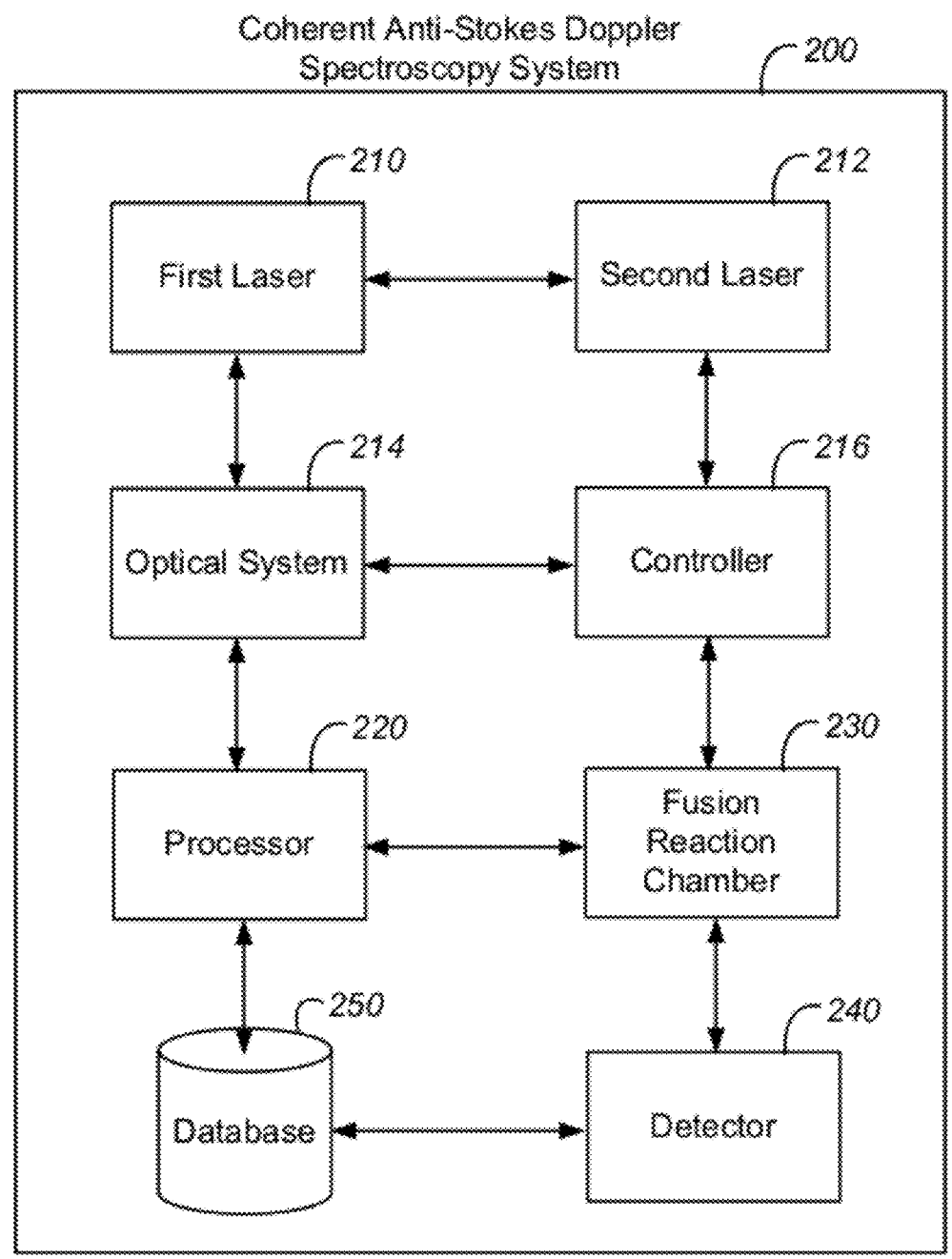
FIG. 2 is a simplified schematic diagram of a coherent anti-Stokes Doppler spectroscopy system according to an embodiment of the present invention.

FIG. 2 is a simplified schematic diagram of a coherent anti-Stokes Doppler spectroscopy system according to an embodiment of the present invention. The system 200 includes a first laser 210 and a second laser 212. Although first laser 210 and second laser 212 are illustrated as separate laser systems in FIG. 2, this is not required by embodiments of the present invention. In some embodiments, a single laser, a beam splitter, and a doubling crystal are utilized to provide to laser beams at different wavelengths. In another embodiment, a single laser system outputting two different laser wavelengths is utilized in place of the two separate systems illustrated in FIG. 2. Thus, embodiments of the present invention, as described more fully below, utilize laser beams at two wavelengths, which can be provided by first laser 210 and second laser 212 as illustrated in FIG. 2 or by other appropriate laser systems. One of ordinary skill in the art would recognize many variations, modifications, and alternatives.

The system 200 also includes an optical system 214 and a controller 216. The optical system, which typically includes lenses, filters, shutters, mirrors, and/or the like, directs the laser beam from the first laser 210 and the laser beam from the second laser 212 into the fusion reaction chamber 230. The optical system is typically disposed external to the fusion reaction chamber 230 but can also include optical elements internal to the fusion reaction chamber. The controller is coupled to both the optical system, for example, to operate shutters, as well as the first laser and the second laser. Thus, control for laser power, wavelength, pulse width, pulse shape, repetition rate, and the like are provided as part of system 200.

The interaction of the first laser beam and the second laser beam will result in conversion of at least of portion of the beams into a coherent anti-Stokes component at $\omega_{AS}=2\omega_1-\omega_2$ as a result of the nonlinear dielectric properties of the noble gas, in this example, xenon. Embodiments of the present invention are not limited to use with xenon, but other noble gases are included within the scope of the present invention. The intensity of the coherent anti-Stokes signal will be proportional to the third-order optical susceptibility ($\chi_3$) and xenon has a relatively high value of $\chi_3$. Thus, embodiments of the present invention provide a signal generated through a non-linear process dependent on the third-order optical susceptibility.

The system 200 includes a processor 220, a database 250, and a detector 240. These elements work in concert to detect the Doppler broadened signal associated with the coherent anti-Stokes component at $\omega_{AS}$. The detector, which has a bandwidth greater than the Doppler broadened linewidth, detects the coherent anti-Stokes signal produced through the nonlinear interaction with the noble gas. The detector can be a photodiode, a CCD, or the like. The signal is processed using processor 220 and database 250 to determine the value of the Doppler broadening. The processor is also used to determine the temperature of the noble gas using the value of the Doppler broadening. One of ordinary skill in the art would recognize many variations, modifications, and alternatives.

Figure 3:
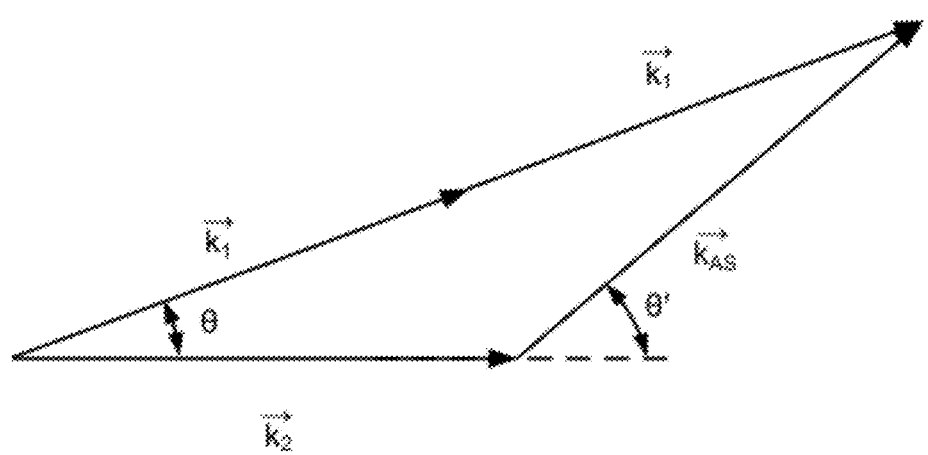
FIG. 3 is a wave vector diagram for phase matching according to an embodiment of the present invention.

FIG. 3 is a wave vector diagram for phase matching according to an embodiment of the present invention. As illustrated in FIG. 3, the coherent anti-Stokes beam is emitted at an angle $\theta'$ along an optical path coupled to detector 240. The linewidth of the coherent anti-Stokes beam is Doppler broadened as a function of the temperature of the gas. Thus, the Doppler broadening of the coherent anti-Stokes beam provides a mechanism for measuring the temperature of the monatomic gas in the fusion reaction chamber.

As illustrated in FIG. 3, phase matching ($\Delta k=0$) is achieved at an angle $\theta$ at which the first laser beam at the first frequency ($v_1$) and the second laser beam at the second frequency ($v_2$) cross (i.e., the phase matching angle). The phase matching angle is determined as illustrated in FIG. 3, where $$|\vec{k}| = \frac{\omega \cdot n}{c} = \frac{2\pi v \cdot n}{c}.$$

According to embodiments of the present invention, the coherent anti-Stokes Doppler beam emerges at a second angle $\theta'$, which promotes spatial filtering of the Doppler beam with respect to the first laser beam and the second laser beam. As discussed above, the coherent anti-Stokes beam has a linewidth that is Doppler broadened due to the temperature of the noble gas.

The inventors have determined that noble gases have relatively high values of $\chi_3$ and will, therefore, still produce an anti-Stokes signal based on the non-linear interaction. While no Raman vibrational structure would be produced by interaction with monatomic species, the anti-Stokes signal will be broadened due to the thermal motion of the gas to produce a Doppler broadened signal. Utilizing the system illustrated in FIG. 2, the Doppler broadening can be measured and used to determine the temperature of the monatomic gas.

Embodiments of the present invention utilize pump beams with predetermined wavelengths in order to produce an anti-Stokes signal at wavelengths that either avoid (non-resonant coherent anti-Stokes signal) or coincide (resonant coherent anti-Stokes signal) with emission lines of the species under test. As an example, in one embodiment, the wavelength of the first beam ($\lambda_1$) is 532 nm ($\omega_1=14.64$ rad) and the wavelength of the second beam ($\lambda_2$) is 1064 nm ($\omega_2=7.32$ rad) in one embodiment, producing an anti-Stokes signal at 355 nm ($\omega_{AS}=2\omega_1-\omega_2$). In other embodiments, the wavelengths of the various beams are selected to provide interaction between beams and the sample as appropriate to the particular application. In some embodiments, one or more tunable lasers are utilized to tune the wavelength of the radiation to the resonance of the gas being analyzed. In an embodiment, a first laser is tuned over the resonance feature while a second laser spanning the resonance feature is utilized in conjunction with the first tunable laser.

Some embodiments of the present invention utilize the Doppler broadening of the coherent anti-Stokes signal to determine the temperature of noble gases in a fusion reaction chamber. Other embodiments utilize the coherent anti-Stokes signal to measure ionized species in a plasma or trace levels in a gas mixture. As an example, by tuning the wavelength of the coherent anti-Stokes signal to an emission line of the gas being measured, trace levels of the gas being measured could be detected. One of ordinary skill in the art would recognize many variations, modifications, and alternatives.

According to some embodiments, the laser sources utilized in generating the coherent anti-Stokes beam have a pulse width of sufficient length to provide an accurate measurement of the Doppler broadening. In implementations of LIFE in which the repetition rate is 13 Hz, the time between fusion events is about 76 ms. Thus, embodiments of the present invention can utilize lasers with pulse widths in the nanosecond range to measure Doppler broadening in the GHz range. It will be appreciated by one of skill in the art will appreciate the longer pulse widths will provide finer temporal resolution for the measurements. Pulse widths in the millisecond range can be suitable for high resolution spectral measurements and shorter pulses are also useful in embodiments of the present invention. If the laser pulse width is on the order of 1 ns, resolution on the order of 1 GHz is available. For a 5 ns pulse, the transform limit is on the order of 200 MHz, which should be useful in resolving a 1 GHz broadening in the Doppler broadened signal.

Figure 4:
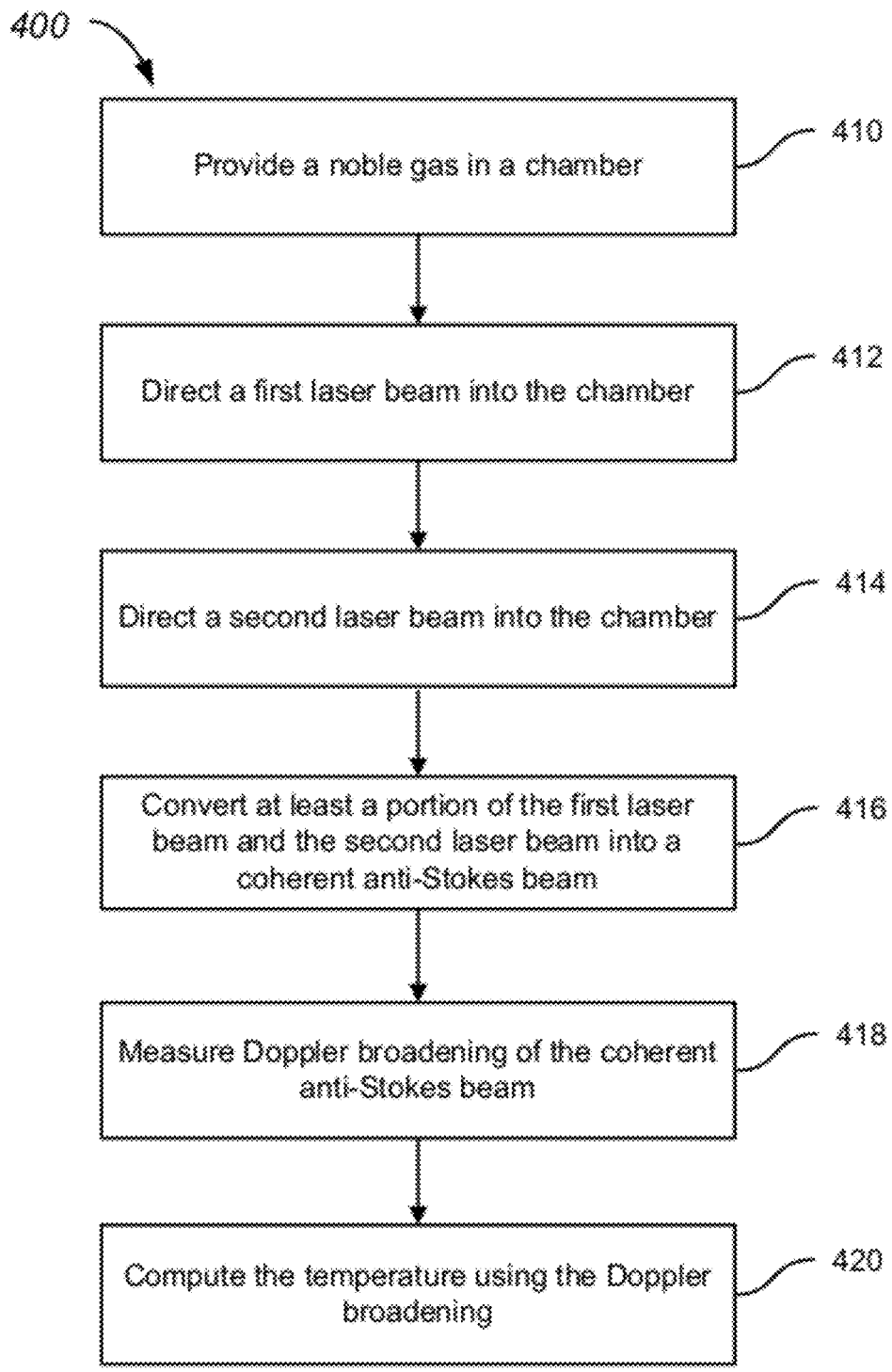
FIG. 4 is a simplified flowchart illustrating a method of measuring gas temperature according to an embodiment of the present invention.

FIG. 4 is a simplified flowchart illustrating a method of measuring gas temperature (e.g., temperature of a noble gas in a chamber) according to an embodiment of the present invention. The method 400 includes providing the noble gas in the chamber (410). The noble gas is characterized by a pressure and a temperature. As an example, the noble gas can be xenon, krypton, a mixture of xenon and krypton, or the like. In fusion reaction chambers, the xenon gas is typically in a plasma state as a result of the high operating temperature of the fusion reaction chamber. The method also includes directing a first laser beam into the chamber (412) and directing a second laser beam into the chamber (414). The first laser beam is characterized by a first frequency and the second laser beam is characterized by a second frequency. The first laser beam and the second laser beam can be pulsed, CW, quasi-CW, or the like.

The method further includes converting at least a portion of the first laser beam and the second laser beam into a coherent anti-Stokes beam (416) and measuring a Doppler broadening of the coherent anti-Stokes beam (418). In an embodiment, the coherent anti-Stokes beam is characterized by a wavelength equal to twice the first frequency less the second frequency. The Doppler broadening of the coherent anti-Stokes beam results from the high temperature of the noble gas and the method also includes computing the temperature of the noble gas using the Doppler broadening (420).

Embodiments of the present invention are useful in measuring the temperatures of noble gases at temperatures ranging from about 500 K to about 10,000 K, for example, in a temperature range from about 600 K to about 1,000 K. Additionally, embodiments of the present invention are useful in measuring the temperatures of noble gases at pressures ranging from about 0.1 Torr to about 1 Torr.

It should be appreciated that the specific steps illustrated in FIG. 4 provide a particular method of measuring gas temperature according to an embodiment of the present invention. Other sequences of steps may also be performed according to alternative embodiments. For example, alternative embodiments of the present invention may perform the steps outlined above in a different order. Moreover, the individual steps illustrated in FIG. 4 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 5:
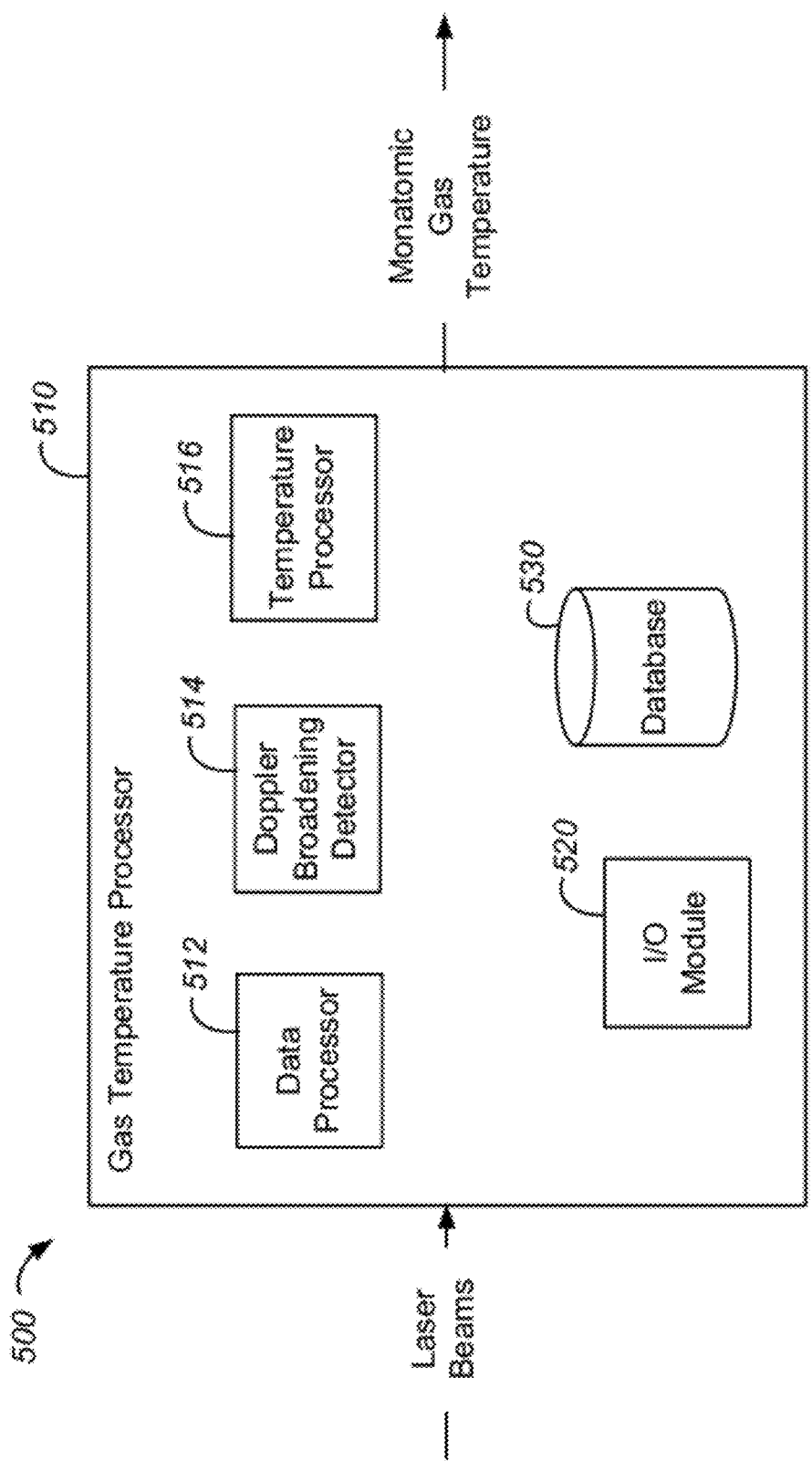
FIG. 5 is a simplified schematic diagram of a noble gas temperature measurement system according to an embodiment of the present invention.

FIG. 5 is a simplified schematic diagram of a noble gas temperature measurement system according to an embodiment of the present invention. The system 500 receives inputs of two laser beams, directed into a chamber using an optical system and an optional controller. The system 500 includes a gas temperature processor 510, which includes a data processor 512 and a Doppler broadening detector 514, which is used to determine the linewidth broadening associated with a coherent anti-Stokes beam produced through a nonlinear interaction with the gas being measured. The linewidth broadening is used as an input to the temperature processor 516 that provides an output including the monatomic gas temperature.

The functionality of the gas temperature measurement system 500 can also be implemented, in part, by an input/output module 520 and a database 530, which can work in conjunction with either the data processor 512, the Doppler broadening detector 514 and/or the temperature processor 516.

The data processor 512 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the present invention in software, firmware and/or hardware. As an example, such processors include dedicated circuitry, ASICs, combinatorial logic, other programmable processors, combinations thereof, and the like. Similarly, temperature processor 516 may be implemented using similar hardware, software, firmware, and the like. In a particular embodiment, the data processor 512 and the temperature processor 516 are combined as a single processor. One of ordinary skill in the art would recognize many variations, modifications, and alternatives.

The database 530 can be local or distributed as appropriate to the particular application. Database 530 may include a number of memories including a main random access memory (RAM) for storage of instructions and data during program execution and a read only memory (ROM) in which fixed instructions are stored. Thus, database 530 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of measuring a temperature of a noble gas in a chamber, the method comprising:
   providing the noble gas in the chamber, wherein the noble gas is characterized by a pressure and a temperature;
   directing a first laser beam into the chamber, wherein the first laser beam is characterized by a first frequency;
   directing a second laser beam into the chamber, wherein the second laser beam is characterized by a second frequency;
   converting at least a portion of the first laser beam and the second laser beam into a coherent anti-Stokes beam;
   measuring a Doppler broadening of the coherent anti-Stokes beam; and
   computing the temperature using the Doppler broadening.

2. The method of claim 1 wherein the noble gas comprises xenon.

3. The method of claim 2 wherein the noble gas comprises a mixture of xenon and krypton.

4. The method of claim 2 wherein the xenon is present in a plasma state.

5. The method of claim 1 wherein the chamber comprises a fusion reaction chamber.

6. The method of claim 1 wherein the temperature ranges from about 500 K to about 10,000 K.

7. The method of claim 6 wherein the temperature ranges from about 600 K to about 1,000 K.

8. The method of claim 1 wherein the pressure ranges from about 0.1 Ton to about 1 Ton.

9. The method of claim 1 wherein the first laser beam comprises a pulsed laser beam and the second laser beam comprises a pulsed laser beam.

10. The method of claim 1 wherein the coherent anti-Stokes beam is characterized by a frequency equal to twice the first frequency less the second frequency.

* * * * *